United States Patent [19]

Accardi

[11] Patent Number: 4,793,001
[45] Date of Patent: Dec. 27, 1988

[54] FULL FACIAL SHIELD ASSEMBLY

[75] Inventor: Vito A. Accardi, Dix Hills, N.Y.

[73] Assignee: Accardi Enterprises, Inc., Dix Hills, N.Y.

[21] Appl. No.: 174,592

[22] Filed: Mar. 29, 1988

[51] Int. Cl.⁴ .............................................. A42B 5/00
[52] U.S. Cl. ................................................................ 2/9
[58] Field of Search ........................................ 2/7, 8, 9

[56] References Cited

U.S. PATENT DOCUMENTS

| | | | |
|---|---|---|---|
| 2,606,321 | 12/1952 | Malcom, Jr. | 2/8 |
| 2,658,200 | 11/1953 | Bowers, Sr. | 2/8 |
| 2,731,637 | 1/1956 | Kaplan et al. | 2/9 |
| 2,758,307 | 8/1956 | Treiber | 2/9 |
| 2,786,204 | 3/1957 | Simpson | 2/9 |
| 2,801,420 | 8/1957 | Malcom, Jr. | 2/9 |
| 2,829,374 | 4/1958 | Malcom, Jr. | 2/9 |
| 2,881,443 | 4/1959 | Barker, Jr. | 2/9 |
| 3,152,888 | 10/1964 | Rogowski | 2/9 X |
| 3,214,767 | 11/1965 | Weber | 2/9 |
| 3,308,477 | 3/1967 | Boyd | 2/9 X |
| 3,310,709 | 3/1967 | Phillips | 2/9 X |
| 3,868,727 | 3/1975 | Paschall | 2/8 |
| 4,694,507 | 9/1987 | Owen | 2/9 X |
| 4,707,860 | 11/1987 | Holmström | 2/8 |

Primary Examiner—Werner H. Schroeder
Assistant Examiner—Jeanette E. Chapman
Attorney, Agent, or Firm—Peter C. Michalos

[57] ABSTRACT

A facial shield assembly for use by dental and medical personnel comprises a transparent plastic shield having a substantially flat front portion and a peripheral border portion extending continuously around the front portion to cover and embrace at least part of a wearer's face. Concave groove structures are provided at the sides of the peripheral border portion to receive a U-shaped band. The groove structures are held on the band by clips which embrace the groove structure. The groove structure and clips have converging walls so that the clip can be wedged onto the groove structures to hold them onto the support band.

20 Claims, 2 Drawing Sheets

U.S. Patent   Dec. 27, 1988   Sheet 1 of 2   4,793,001
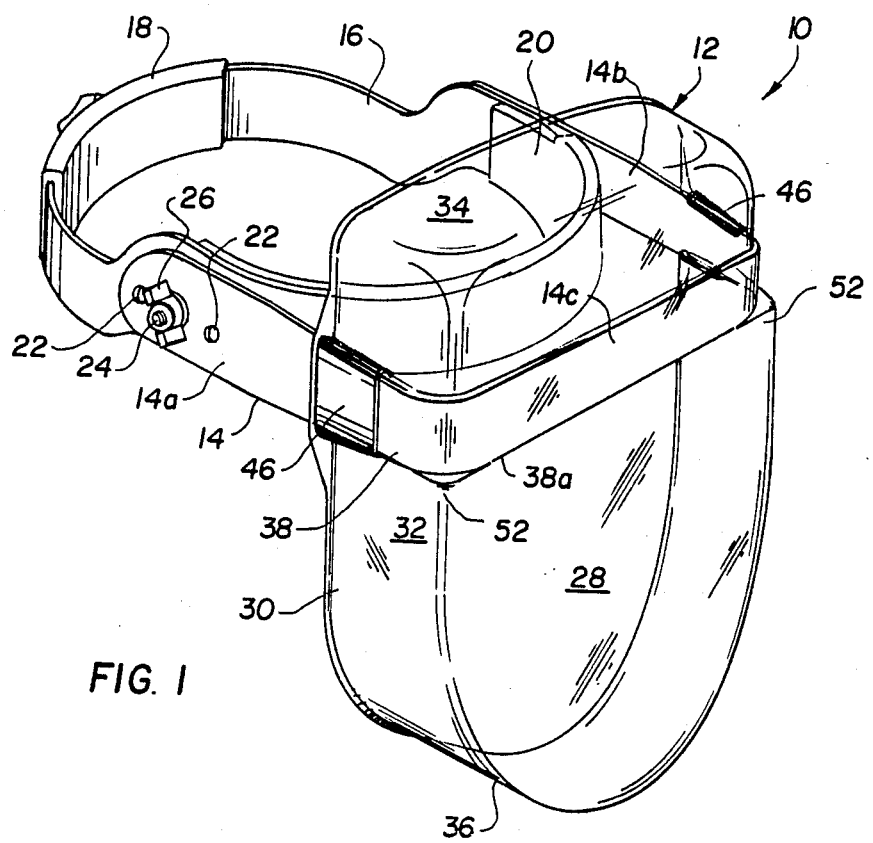
FIG. 1
FIG. 2
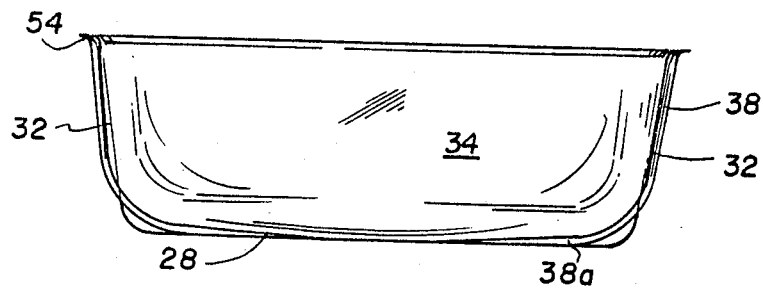

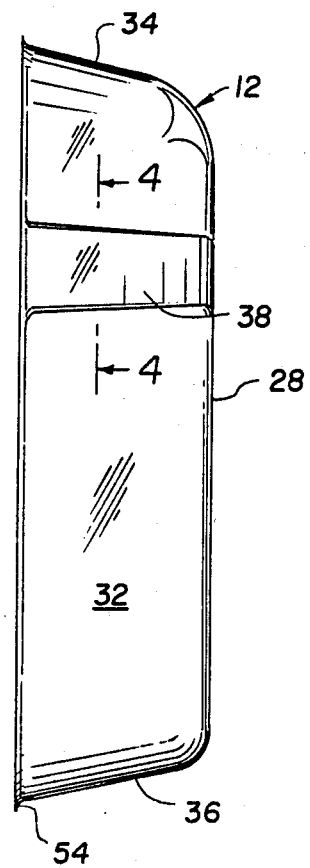
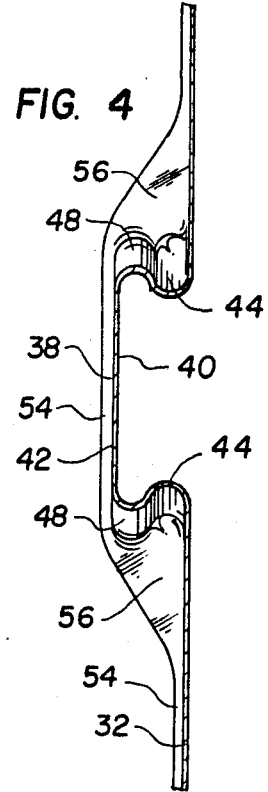
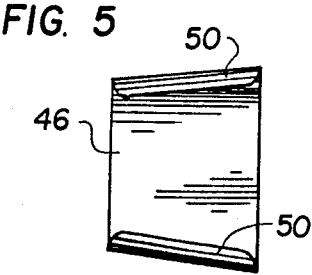
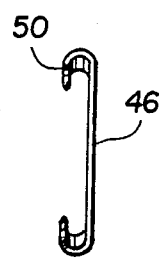
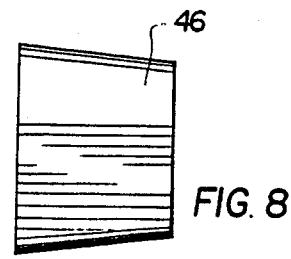

FULL FACIAL SHIELD ASSEMBLY

FIELD AND BACKGROUND OF THE INVENTION

The present invention relates in general to protective eye and face shields, and, in particular, to a new and useful facial shield for dental and medical use to shield the face of a practitioner from splatter, droplets and aerosol.

Practitioners in the field of dentistry have become increasingly aware of the possible dangers of contamination through splatter, droplets and aerosols, which may contain contagions from a patient. This concern has spread to the general medical community as the dangers of contracting diseases, such as herpes, hepatitis and aids, increase.

An article entitled "Controlling Aerosols, Splatter, Droplets" by Teri Reis-Schmidt, Dental Products Report, March 1988, analyzes the current thinking on protective attire for dental personnel. The article observes that high speed cutting instruments and ultrasonic scalers tend to produce splatter and aerosols in the operatory. Splatter droplets are defined as measuring more than fifty micrometers in diameter, while aerosols are defined as air suspended liquid or solid particles that measure less than fifty micrometers in diameter. Bacterial cells average one micrometer in diameter, while virus are considerably smaller. The article states that particles measuring less than five micrometers can penetrate lung passages all the way to the alveoli if they are inhaled.

While it is debated whether aerosols are capable of transmitting diseases, such as hepatitis B, it was observed in the article that common airborne aerosols should be differentiated from aerosols produced by high speed and high frequency equipment commonly used by a dentist, which aerosols may contain saliva and blood. While some experiments show that aerosolized blood and saliva from dental equipment does not transmit contagions, other experiments show that a simple cough or sneeze may produce airborne colony forming units of bacteria.

Diseases which can be transmitted via droplets from dental patients are identified by the article as including the common cold, hepatitis B, non-A/non-B hepatitis, influenza, measles (German and Rubeola), tuberculosis, staphylococcus and streptococcus infections and herpes infections, such as chicken pox (herpes zester), infectious mononucleosis (Epstein-Barr virus), herpetic whitlow (herpes simplex type I) and herpetic conjunctivitis (herpes simplex type I). Diseases that can be transmitted by respiratory roots include Legionellosis, mumps and pneumonia.

Despite the ongoing debate on which diseases can be transmitted through droplets, splatter or aerosols, it has become increasingly apparent that reasonable safety measures must be taken.

Although common eye wear, such as prescription glasses, may provide a modicum of protection, splatter and aerosol can easily circumvent such eye wear and contact the eyes of the practitioner. Such eye wear, of course, leaves the remainder of the face and, in particular, the nostrils and mouth, unprotected. Contamination to the practitioner's hair must also be considered.

Currently, face shields are known which cover the front, and wrap partially to the side of a practitioner's face. One shield, which was invented by the present inventor, even wraps partly around the bottom of the shield to provide some chin protection.

To be practical, however, all face shields must be sterilizable. This becomes increasingly difficult as the face shields become complex in structure. To be practical, the shields must also be perfectly transparent and optically non-distorting.

To dare, no full facial shield has all of the foregoing required attributes.

SUMMARY OF THE INVENTION

The present invention comprises a full facial shield for use by dental and medical practitioners, which provides a perfectly transparent viewing area for the practitioner, while providing peripheral protection entirely around the practitioner's face. The facial shield of the present invention can be sterilized by conventional cold chemical or gaseous sterilization techniques.

The facial shield of the present invention is incorporated in a shield assembly including a support band onto which the shield is mounted. The support band is adjustably connected and pivotally mounted on a head band. Adjustment is provided for mounting the shield closer to or further from the practitioner's face to control fogging due to the practitioner's respiration.

Mounting of the shield to the support band is achieved by a wedging action which avoids the need for any permanent hardware on the shield or on the band. No apertures are needed through the shield. By eliminating hardware or apertures which may serve as contamination sites, more complete sterilization of the shield is possible. The ease with which the shield can be disconnected from its supporting assembly also encourages the frequent replacement and sterilization of shield. Since the supporting parts of the assembly, including the support and head bands, are less subjected to contamination, they can be cleaned and/or sterilized less frequently.

Accordingly, an object of the present invention is to provide a facial shield assembly for dentistry and medicine which comprises a transparent facial shield, having a front portion adapted to cover the front of a wearer's face, two temple portions extending from the front portion, a bottom chine portion extending from the front portion and a top crown portion extending from the front portion. The temple, top and bottom portions form a continuous peripheral border around the front portion, thus protecting the wearer's chin, temples, forehead and part of the wearer's hair beyond the hairline.

A further object of the invention is to provide a groove structure in the temple portions, which include a concave surface on one side and a convex surface on the opposite side. A support band engages in the concave surface of the groove structure. The shield is held to the support band by wedging clips which squeeze the groove structure against the support band. Removal of the shield is possible by simply removing the clips and disengaging the shield from the support band.

Another object of the present invention is to provide a head band for pivotally supporting the support band, the support band being mounted at an adjustable position on the head band for adjusting the distance between the face shield and the wearer's face.

A still further object of the present invention is to provide a face shield which is perfectly clear at least through its front portion and which is made of material that can be sterilized.

Another object of the present invention is to provide a facial shield assembly which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS In the drawings:

FIG. 1 is a perspective view of the inventive full facial shield assembly;

FIG. 2 is a top plan view of the face shield used in the assembly of FIG. 1;

FIG. 3 is a side elevational view of the face shield;

FIG. 4 is a sectional view taken on line 4—4 of FIG. 3, showing the groove structure of the face shield;

FIG. 5 is a side elevational view showing the inside of a wedging clip used to hold the face shield to the facial shield assembly;

FIG. 6 is a top plan view of the clip shown in FIG. 5;

FIG. 7 is an end elevational view of the clip shown in FIG. 5; and

FIG. 8 is a side elevational view of the clip showing the exterior surface thereof.

DESCRIPTION OF THE PREFERRED EMBODIMENT

Referring to the drawings in particular, the invention embodied in FIG. 1 comprises a full facial shield assembly generally designated 10, having a transparent face shield generally designated 12 mounted on a support band 14, which is pivotally and adjustably connected to a head band 16.

Head band 16 is of conventional design and includes an adjustment mechanism 18 for adjusting the inside diameter of the head band, as well as padding 20 for engaging the temples and forehead of a wearer.

Support band 14 includes side temple parts 14a and 14b and a frontal part 14c. Support band 14 is generally U-shaped with generally flat temple parts 14a, 14b and substantially straight or only slightly curved frontal part 14c.

To adjust the distance between face shield 12 and the face of a wearer, the temple parts are provided with adjustment means in the forms of plural holes 22 through each temple part. In the case shown in FIG. 1, the central hole receives a bolt 24 which is fixed to head band 16. A wing nut 26 is threaded onto bolt 24 and frictionally holds temple part 14a against the surface of head band 16. Advantageously, bolt 24 and nut 26 are made of nylon. By either increasing or decreasing the frictional engagement between the support band 14 and head band 16, the wearer can adjust the amount of pressure needed to raise and lower the face shield. In this way, when the wearer is not treating a patient, the shield can be pivoted up away from the wearer's face while the assembly remains on the wearer's head.

Face shield 12 comprises a front portion 28 which is perfectly transparent and substantially flat. A peripheral border 30, which is made as one piece with the frontal portion 28 extends all the way around the periphery of the front portion and toward the wearer's face. Border 30 includes a pair of opposite side portions 32 for providing a guard against aerosols or droplets invading from the sides, a top crown portion 34 for protecting the forehead and part of the hairline of the wearer and a bottom chin portion 36 for the chin area of the wearer.

Referring to FIGS. 3 and 4, the face shield 12 also includes a pair of groove structures 38, each extending along one side portion 32. Each groove structure 38 also has a part 38a (see FIG. 2), which extends partly onto the front portion 28 of the face shield 12.

Groove structures 38 are provided for receiving the support band 14 at a location above the level of the wearer's eyes. As best shown in FIG. 4, each groove structure 38 has an interior concave surface 40 and an exterior convex surface 42. Groove structure 38 also includes a pair of overhanging ridges 44 at the top and bottom of the concave surface for at least partly embracing the temple parts 14a and 14b of the support band 14. To positively fix the shield 12 to the support band, wedging clips 46 are slipped over the outer convex surface 42 of each groove structure 38 and are forced into wedging engagement with outer ridges 48 of the groove structure 38. Since the shield 12 is made of resilient plastic material, clips 46 compress the ridges 48 against the support band 14, thus fixing the shield to the support band.

To this end, side edges of the temple parts 14a and 14b, as well as the ridges 48 and 44 diverge in a direction away from the front portion 28 of shield 12.

The structure of wedging clips 46 is shown in FIGS. 5 through 8. Each wedging clip includes a pair of spaced apart rails 50, which define inner slots that converge with each other and which receive the ridges 48.

Face shield 12 is advantageously made of crystal clear plastic material, such as PETG plastic which can be repeatedly sterilized, using either the cold chemical sterilization technique, normally used for sterilizing dental equipment, or a gaseous sterilizing technique widely used by large institutions, such as the Veterans Administration. Gaseous sterilization involves immersion into an ethylene oxide environment at a temperature of about 112° F. for a period of about eight hours.

To preserve the distortion free crystal clarity of the front portion 28 of shield 12, convex cheek portions 52 are provided below groove structures 38 at the transition area between the front portion 28 and the peripheral border 30 of face shield 12. In view of the fact that the groove structure is positioned above the eyes of a wearer, cheek portions 52 provide the largest, flattest window area on front portion 28 for an un-obstructed view of the patient. This avoids distortion which is sometimes due to the bending of transparent plastics, which may occur, for example, at the curved transition areas between the front portion 28 and the border 30.

A flange 54 extends around the exposed edge of border 30. Flange 54 extends over the edge of groove structure 38, as shown in FIG. 4 and includes webs 56 between side portions 32 and the groove structure 38. Webs 56 act both to reinforce the groove structure 38 and, in conjunction with flange 58, act as a stop for wedging clips 46. This avoids pushing wedging clips 46 too deeply onto groove structures 38, which may hamper the easy removal of the clips and shield and which further might damage the shield.

Wedging clips 46 are advantageously made of stainless steel. Again, to prevent damage to the flexible plastic shield 12, rails 50 have rounded edges.

While a specific embodiment of the invention has been showed and described in detail to illustrate the application of the principles of the invention, it will be understood that the invention may be embodied otherwise without departing from such principles.

The invention claimed is:

1. A dental and medical facial shield assembly comprising:
   a transparent face shield having a front portion adapted to cover the front of a wearer's face and a peripheral border around the front portion and adapted to extend toward the periphery of a wearer's face, said front portion and peripheral border defining an interior space, said face shield including a pair of spaced apart groove structure in said peripheral border, each groove structure having a concave surface on one side thereof and a convex surface on an opposite side thereof;
   a support band for engagement in at least one of said groove structures for engaging the concave surface of said at least one of said groove structure to support said face shield; and
   a clip engaged over said at least one groove structure and engaged against said convex surface of said at least one groove structure for holding said face shield to said support band.

2. An assembly according to claim 1, wherein said support band is substantially U-shaped and engages both of said groove structures, said assembly including a further clip with each of said first-mentioned and further clips engaged to one of said groove structures for holding said face shield to said support band.

3. An assembly according to claim 2, including a head band, said support band comprising a pair of temple parts connected to a frontal part, each temple part being pivotally connected to said head band.

4. An assembly according to claim 3, including adjustment means connected between each temple part of said support band and said head band for adjusting a distance between said face shield and said head band.

5. An assembly according to claim 1, wherein said groove structure comprises a pair of spaced apart ridges for receiving said support band, said ridges diverging from each other, said clip comprising a wedging clip having rails for receiving said ridges, said rails diverging from each other.

6. An assembly according to claim 5, wherein said ridges for receiving said support band comprise outer ridges, said groove structure including inner overhanging ridges overhanging said outer ridges defining slots for receiving said rails of said wedging clip.

7. An assembly according to claim 6, wherein said groove structure has an outer edge spaced away from said front portion of said face shield and a flange at said outer edge acting as a stop for movement of said wedging clip on said groove structure.

8. An assembly according to claim 7, wherein said border includes an outer edge spaced from said front portion, said flange extending around said border outer edge and a web formed in said flange from said border to said groove structure for reinforcing said groove structure.

9. An assembly according to claim 1, wherein said peripheral border comprises a pair of side portions, a top crown portion connected between said side portions at a top of said front portion and a bottom chin portion connected between said side portions at a bottom of said front portion, and of said groove structures being formed on each of said side portions and extending at least partly onto said front portion.

10. An assembly according to claim 9, wherein said concave surface of each groove structure communicates with the interior space of said face shield.

11. An assembly according to claim 9, including a convex cheek portion extending outwardly from each groove structure at a location below each groove structure and at a transition area between said front portion and each of said side portions, for rendering said front portion below said groove structures substantially flat.

12. An assembly according to claim 1, wherein said face shield is made of sterilizable plastic and is free of apertures.

13. An assembly according to claim 1, wherein said groove structure has an edge spaced away from said front portion and a flange on said edge acting as a stop for said clip.

14. An assembly according to claim 13, wherein said groove structure has ridges on opposite sides of said convex surfaces for receiving said support band, said ridges converging toward each other.

15. A full facial shield comprising:
    a transparent front portion of a size adapted to cover the front of a wearer's face;
    a peripheral border made as one piece with said front portion and extending around said front portion in a direction adapted to engage around at least part of the wearer's face, said border including a pair of said portions, a top crown portion connected between tops of said side portions and a bottom chin portion connected between bottoms of said side portions; and
    a groove structure in each of said side portions at a level adapted to be above the eyes of a wearer, each groove structure being concave on an inner surface of said side portion for engaging a supporting band.

16. A shield according to claim 15, wherein each groove structure extends at least partly into said front portion, each groove structure having side ridges which converge toward each other in a direction away from said front portion.

17. A shield according to claim 16, wherein each ridge comprises an outer concave ridge, each groove structure including an inner convex ridge overhanging said outer concave ridge, and defining a rial slot for receiving the rail of a clip adapted to hold said groove structure to a supporting band.

18. A shield according to claim 17, including a convex cheek portion in said face shield below each of said groove structures and at a location of intersection between said front portion and each side portion, said front portion being substantially flat at a location below said groove structures and into at least part of the area of each cheek portion.

19. A shield according to claim 16, wherein said border includes an outer edge spaced away from said front portion and a flange extending around said outer edges and over said groove structures.

20. A shield according to claim 19, including a web formed as part of said flange at locations above and below each of said groove structures.

* * * * *